US012599442B2

(12) United States Patent　　　(10) Patent No.: US 12,599,442 B2
Noorizadeh et al.　　　　　　　　 (45) Date of Patent: Apr. 14, 2026

(54) ASSISTIVE SURGICAL ROBOT FOR DISTAL HOLE LOCALIZATION IN INTRAMEDULLARY NAIL

(71) Applicant: QATAR UNIVERSITY, Doha (QA)

(72) Inventors: Mohammad Noorizadeh, Doha (QA); Nader Meskin, Doha (QA); Masoud Noorizadeh, Doha (QA)

(73) Assignee: Qatar University, Doha (QA)

( * ) Notice: Subject to any disclaimer, the term of this patent is extended or adjusted under 35 U.S.C. 154(b) by 1118 days.

(21) Appl. No.: 17/582,629

(22) Filed: Jan. 24, 2022

(65) Prior Publication Data

US 2022/0233256 A1　　Jul. 28, 2022

Related U.S. Application Data

(60) Provisional application No. 63/141,352, filed on Jan. 25, 2021.

(51) Int. Cl.
| | |
|---|---|
| *A61B 34/30* | (2016.01) |
| *A61B 6/12* | (2006.01) |
| *A61B 17/16* | (2006.01) |
| *A61B 17/84* | (2006.01) |

(52) U.S. Cl.
CPC ............... *A61B 34/30* (2016.02); *A61B 6/12* (2013.01); *A61B 17/164* (2013.01); *A61B 17/846* (2013.01)

(58) Field of Classification Search
CPC ......... A61B 34/10; A61B 34/20; A61B 34/25; A61B 34/30; A61B 17/164; A61B 17/846; A61B 6/12
See application file for complete search history.

(56) References Cited

U.S. PATENT DOCUMENTS

| | | | | |
|---|---|---|---|---|
| 10,849,711 B2 * | 12/2020 | Mata | .................. | A61B 17/1703 |
| 2008/0091101 A1 * | 4/2008 | Velusamy | .......... | A61B 10/0233 |
| | | | | 600/427 |
| 2018/0256259 A1 * | 9/2018 | Crawford | ........... | A61B 17/7082 |
| 2018/0296285 A1 * | 10/2018 | Simi | ......................... | B25J 3/04 |
| 2021/0077126 A1 * | 3/2021 | Karg | ................. | A61B 17/1725 |
| 2021/0282866 A1 * | 9/2021 | Vij | ............................ | G06T 7/20 |

* cited by examiner

*Primary Examiner* — Si Ming Ku
(74) *Attorney, Agent, or Firm* — Hodgson Russ LLP

(57) ABSTRACT

A system for robot assisted surgery can include an imaging device configured to capture an image of an implanted device and a probe. The implanted device can define a hole and the probe can define a hole. The system can also include a robot configured to align a fastener to the hole defined by the implanted device. The system can further include at least one memory that includes computer program instructions and at least one processor. The at least one memory and the computer program instructions can be configured to, with the at least one processor, perform obtaining a position and orientation of the hole defined by the implanted device. The at least one memory and the computer program instructions can also be configured to, with the at least one processor, perform aligning the fastener to the hole using the obtained position and orientation.

18 Claims, 8 Drawing Sheets

110

120　　　130

One X-ray image $x_h, y_h, z_h, \theta_h$

Not Perfect
Circle

Perfect
Circle

Table 1

| Hole | Centriod (pixel) | Major Axis Length (pixel) | Minor Axis Length (pixel) |
|---|---|---|---|
| Probe Hole #1 | [1070.4,286.2] | 84.93 | 81.53 |
| Probe Hole #2 | [1216.2,291.2] | 85.7 | 83.5 |
| Distal Hole #1 | [914.1,1780.4] | 20.5 | 12 |
| Distal Hole #2 | [917.1,1972.6] | 18.9 | 10.2 |

Table 2

| Nail Rotation Angle (degree) | Calculated $\theta_h$ (degree) |
|---|---|
| 85 | $\theta_{h1} = 86.56$ and $\theta_{h2} = 85.11$ |
| 80 | $\theta_{h1} = 78.44$ and $\theta_{h2} = 79.05$ |
| 75 | $\theta_{h1} = 75.39$ and $\theta_{h2} = 75.56$ |
| 65 | $\theta_{h1} = 66.62$ and $\theta_{h2} = 64.99$ |

FIG. 11

ASSISTIVE SURGICAL ROBOT FOR DISTAL HOLE LOCALIZATION IN INTRAMEDULLARY NAIL

CROSS-REFERENCE TO RELATED APPLICATION

This application is related to and claims the benefit and priority of U.S. Provisional Patent Application No. 63/141,352, filed Jan. 25, 2021, the entirety of which is hereby incorporated herein by reference.

FIELD

Some example embodiments may generally relate to assistive surgical robots for distal hole localization in intramedullary nail systems, devices, and methods. Some example embodiments may relate to robots and control systems thereof for assisting in surgery involving implantable devices, such as intramedullary nails.

BACKGROUND

In the present century, concern for accuracy in medical procedures has only increased. While numerous improvements have been made, there are many areas of medical practice in which there may be reliance on the expertise and experience of the human surgeon.

Although many experienced surgeons may be able to obtain high quality and high accuracy results based on their expertise and experience, such expertise and experience requires a period of learning. If the period of learning involves performing procedures on human patients, the results may be sub-optimal for patients experiencing the learning portion of the surgeon's practice.

Additionally, in cases where the procedures involve making spatial reasoning estimates of unseen targets, there may be a temptation to use advanced imaging equipment, such as fluoroscopy. While improvements in fluoroscopy have reduced radiation levels needed, producing a live X-ray image may still require many exposures of X-ray radiation for the patient and potentially also for a surgeon or other operating room staff.

SUMMARY

An embodiment may be directed to a system for robot assisted surgery. The system can include an imaging device configured to capture an image of an implanted device and a probe. The implanted device can define a hole and the probe can define a hole. The system can also include a robot configured to align a fastener to the hole defined by the implanted device. The system can further include at least one memory that includes computer program instructions and at least one processor. The at least one memory and the computer program instructions can be configured to, with the at least one processor, perform obtaining a position and orientation of the hole defined by the implanted device. The at least one memory and the computer program instructions can also be configured to, with the at least one processor, perform aligning the fastener to the hole using the obtained position and orientation.

An embodiment may be directed to a method for robot assisted surgery. The method can include capturing, with an imaging device, an image of an implanted device and a probe. The implanted device can define a hole and the probe can define a hole. The method can also include obtaining, by a processor, a position and orientation of the hole defined by the implanted device. The method can further include aligning, by a robot, the fastener to the hole using the obtained position and orientation.

BRIEF DESCRIPTION OF THE DRAWINGS

For proper understanding of example embodiments, reference should be made to the accompanying drawings, wherein:

FIG. 11 illustrates two tables of data from an example implementation.

DETAILED DESCRIPTION

Figure 1:
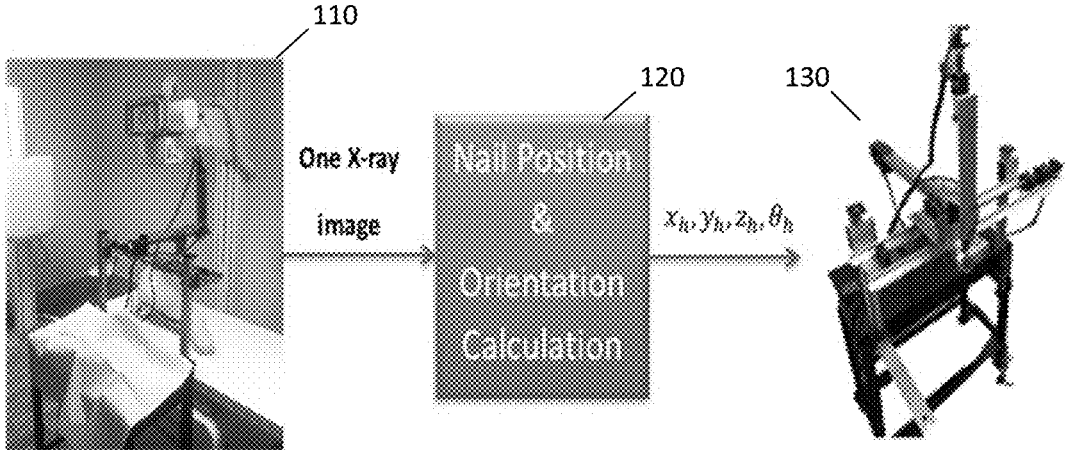
FIG. 1 illustrates an overall schematic of an assistive surgical robot (ASR) for distal hole localization, according to certain embodiments.

It will be readily understood that the components of certain example embodiments, as generally described and illustrated in the figures herein, may be arranged and designed in a wide variety of different configurations. Thus, the following detailed description of some example embodiments of an assisted surgical robot for distal hole localization in an intramedullary nail and associated control systems thereof, is not intended to limit the scope of certain embodiments but is representative of selected example embodiments.

The features, structures, or characteristics of example embodiments described throughout this specification may be combined in any suitable manner in one or more example embodiments. For example, the usage of the phrases "certain embodiments," "some embodiments," or other similar language, throughout this specification refers to the fact that a particular feature, structure, or characteristic described in connection with an embodiment may be included in at least one embodiment. Thus, appearances of the phrases "in certain embodiments," "in some embodiments," "in other embodiments," or other similar language, throughout this specification do not necessarily all refer to the same group of embodiments, and the described features, structures, or characteristics may be combined in any suitable manner in one or more example embodiments.

Certain embodiments may have various aspects and features. These aspects and features may be applied alone or in any desired combination with one another. Other features, procedures, and elements may also be applied in combination with some or all of the aspects and features disclosed herein.

Additionally, if desired, the different functions or procedures discussed below may be performed in a different order and/or concurrently with each other. Furthermore, if desired, one or more of the described functions or procedures may be optional or may be combined. As such, the following description should be considered as illustrative of the principles and teachings of certain example embodiments, and not in limitation thereof.

In certain embodiments, a five degrees-of-freedom assistive surgical robot can localize a distal hole in an intramedullary nail in an internal-fixation surgery using only one X-ray image. Using a specific probe that is connected to the developed robot and can be seen in the X-ray image, the location and orientation of the distal hole can be identified and used for guiding the robot to point accurately to the distal hole in a patient limb. The distal hole orientation can be accurately calculated from the X-ray image with a maximum error of 0.56 degree. The positioning accuracy of the robot may be 0.01 mm and the orientation accuracy of the robot may be 0.5 degree.

In the following discussion, the context of a human patient is used as an example. Nevertheless, intramedullary nails can be used in other vertebrates that have a medullary canal. Additionally, while intramedullary nails are used as an example, the robot of certain embodiments may be configured to control with respect to other implanted devices. While X-ray imaging is used as an example, any other desired imaging technique may be used. In certain embodiments, robots with more or fewer than five degrees of freedom may be used, with five degrees of freedom being used an example.

Intramedullary nails can be used in a variety of medical procedures, including procedures for addressing tibial fractures. Tibial nails are an example of intramedullary nails. Such nails may have locking screw holes close to both ends, in multiple orientations. The nails themselves may be solid, for example, solid stainless steel, such as austenitic 316 stainless or martensitic 440 or 420 stainless. Other metals may also be used. The nails may be cannulated or otherwise hollowed, which may reduce their weight.

After appropriate preparation, which may including reaming of the intermedullary canal, a nail can be inserted either by hand or with gentle hammering. As a result of this process, the distal end of the nail may be within a distal section of the intermedullary canal, surrounded by bone. To fix the distal end of this nail, there may be holes provided near the distal end of the nail. These holes may be provided at multiple orientations and at more than one offset from the end of the nail. Nevertheless, it may be valuable to accurately know the position these holes, so that screws can be inserted into the holes without using a trial and error approach. A trial and error approach could result in unnecessary damage to the distal portion of the bone, as well as other tissues of the patient.

In certain embodiments, rather than relying solely on the manual dexterity and spatial reasoning of a human surgeon, an assistive surgical robot can be used.

Thus, doctors, technicians, and others may be able to use certain embodiments to find distal interlocking holes in bone fracture operations and accurately place screws into these distal interlocking holes. Moreover, in certain embodiments it may be possible to accomplish such a task while minimizing the amount of X-ray radiation used.

The accuracy of the device performing installation of the screws may depend on the motor control of the robot. For example, high precision stepper motors can be used. Moreover, a high precision servo motor and high precision ball-screw can provide accuracy. While these motors may provide certain benefits, the use of other motor types is also permitted.

Certain embodiments may be able to perform the process of interlocking with an interlocking time of less than one minute. Moreover, certain embodiments may be operable with only one X-ray image and 0.01 minutes radiation time. Thus, certain embodiments may be faster and require less radiation than alternative approaches in intramedullary nailing procedure.

Consequently, surgeons and their patients may receive less radiation per year or per surgery. Also, the image can be also taken in the absence of surgeons, which may also lead to minimizing the radiation for surgeons. Certain embodiments may provide such benefits and advantages from the integration of localization and pointing using the assistive surgical robot with the features described herein. Moreover, in previous approaches, the interlocking performance heavily depended on the surgeon's experience. However, in certain embodiments, the assistive surgical robot can automatically find the location of the distal hole, independent from the surgeon experience.

Certain embodiments relate to an assistive surgical robot (ASR) for distal hole localization in the intramedullary nail (IMN) procedure. A five degrees-of-freedom (DoF) robot, according to certain embodiments, can accurately localize the distal holes. The location and orientation of the distal hole can be first obtained using only one X-ray image. A computer-assisted image processing technique and knowledge of the geometry of the distal hole in the nail can provide the location and orientation of the distal hole. Then, based on the obtained information regarding the location and orientation of the distal hole, the robotic arm can accurately locate the distal holes in the nail. Consequently, using the developed localization method and the assistive surgical robot, the radiation exposure for finding the location and orientation of distal screws in the IMN procedure can be significantly decreased. At the same time, the speed of the whole operation can be enhanced.

The ASR may only need a single X-ray for localization, only one-time calibration is needed due to the use of a fixed probe connected to the ASR, and there may be no direct contact with the patient body or bone during the localization. The ASR may include a camera and communication equipment that may be used for remote operation, control, and override of the ASR. For example, the ASR may include a controller that is configured to receive remote commands, such as start and stop, as well as commands such as commands to withdraw. In certain embodiments, the robot may align a fastener, such as a screw, for insertion into a patient's body, or a guide for such a fastener, but the robot may leave insertion of the fastener to a human operator, such as a surgeon.

FIG. 1 illustrates an overall schematic of an assistive surgical robot (ASR) for distal hole localization, according to certain embodiments. As shown in FIG. 1, first the distal hole position and orientation can be obtained using one X-ray image at 110. Then, the position and orientation can be calculated at 120. Then, the calculated position and orientation can be used, at 130, by the developed robot to accurately point to the identified distal hole in the patient limb.

Figure 2:
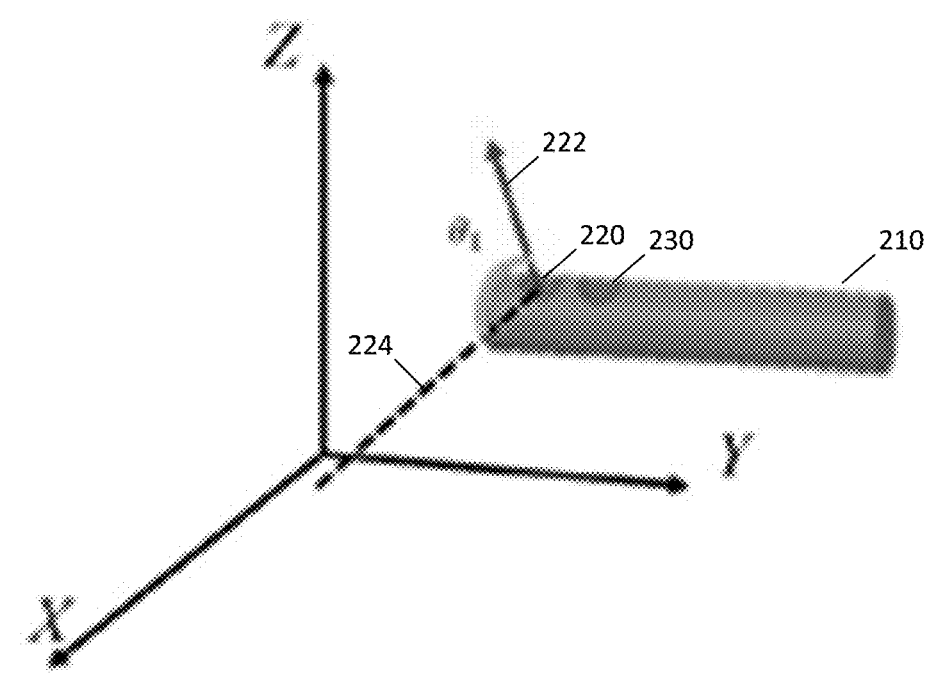
FIG. 2 illustrates a distal hole location and orientation.

FIG. 2 illustrates a distal hole location and orientation. In FIG. 2, a given nail 210 can have a first distal hole 220 and a second distal hole 230. In this example, only the first distal hole 220 may be of interest. A calculation can be made of the position 224 of the first distal hole 220, for example expressed in X, Y, Z coordinates with reference to an origin position. A calculation can also be made of an orientation 222 of the first distal hole 220, which may be expressed in degrees or radians, expressed as $\theta_1$.

During the internal fixation of an intermedullary nail, it is required to both know the location and orientation of the distal hole of the nail in the patient limb. Generally, the distal hole can be represented as a vector in the 3D space at a given location where the vector direction specifies the orientation of the hole. However, due to the specific configuration of the distal hole in the nail and positioning the patient limb parallel to Y axis of the developed robot, the orientation vector is always located in the X-Z plane and hence it can be presented mainly by an angle with respect to the X-axis. Therefore, generally, the required location and orientation information of a given distal hole can be represented by a vector $q=[x_h, y_h, z_h, \theta_h]$ where $p=[x_h, y_h, z_h]$ corresponds to the location of hole and $\theta_h$ is the angle between the positive direction of X axis and the hole orientation vector. The main aim of the developed ASR is both to localize the distal hole using one X-ray image and to point to the distal hole using the obtained orientation in the patient's limb with the ultimate goal to enhance the accuracy of distal hole localization in the intramedullary nailing procedure.

Figure 3:
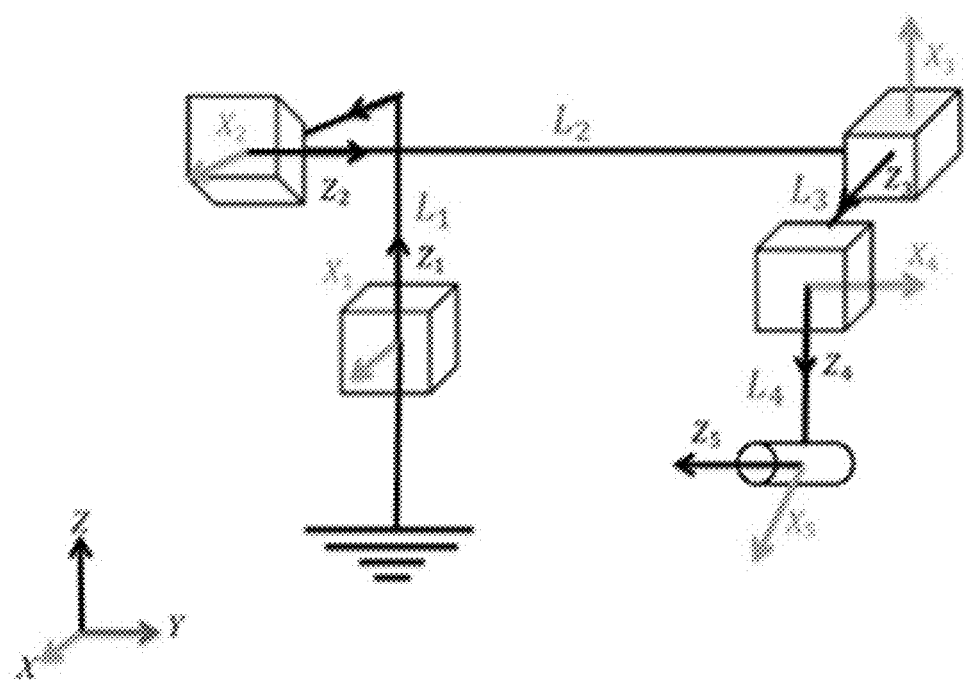
FIG. 3 illustrates an ASR schematic diagram, according to certain embodiments.

FIG. 3 illustrates an ASR schematic diagram, according to certain embodiments. To enhance the accuracy of distal hole localization in the intramedullary nailing procedure, and due to the required work-space for distal hole localization, a 5-degrees-of-freedom ASR can be provided. As shown in FIG. 3, an ASR can have the following configuration: one arm with a prismatic joint in the Y direction ($L_2$), one arm with a prismatic joint in the X direction ($L_3$), two arms with a prismatic joint in the Z direction ($L_1$ and $L_4$) for better accessibility, and one final arm with a revolute joint for pointing to the distal hole. The average length of the human femur bone, which is the longest vertical bone in human body, is about 50 cm. Therefore, by considering 10 cm as the tolerance, the required traveled distance in the Y direction of the ASR can be selected as 60 cm. Similarly, in order to cover all types of the fraction or dislocation, the required traveled distance in the X and Z directions can be selected as 35 cm. Although human bones are an example, an appropriately scaled version of this ASR could be applied to much larger bones. Thus, the values provided are examples. In order to have a linear motion in all the required directions, one can select a linear actuator or a stepper motor with a ball-screw to convert the rotary motion to the linear one.

A linear actuator may not be suitable due to lower accuracy, greater space consumption, and greater cost. Hence, in certain embodiments, four stepper motors along with a ball-screw configuration can be used to provide all the required linear motions. Although using the ball-screw may lead to a speed reduction, a ball-screw can provide high accuracy and robustness, no back-lashing, and a smooth motion without any vibration.

Figure 4:
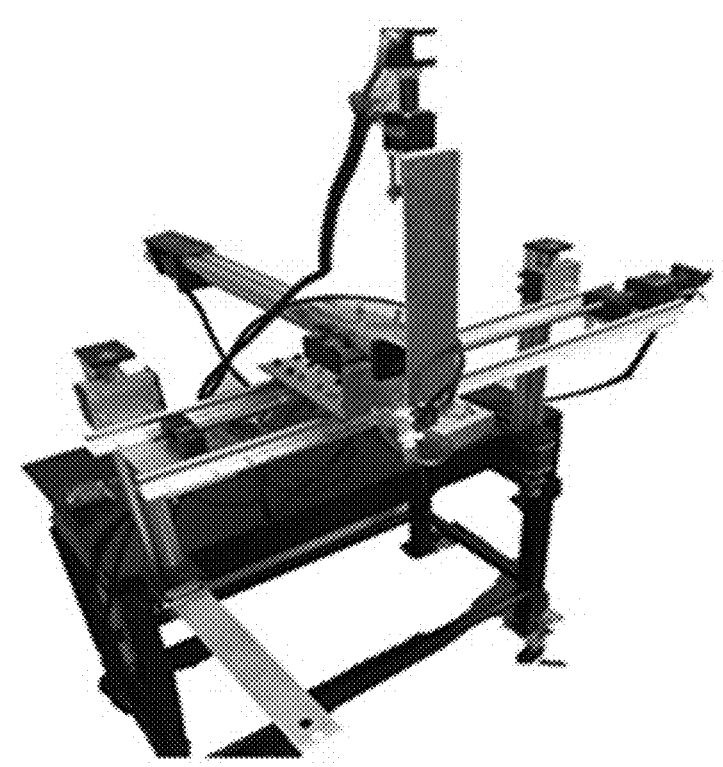
FIG. 4 illustrates a five degree-of-freedom (DoF) ASR, according to certain embodiments.

A small servo motor may be located in link $L_4$ to point to the distal hole with the required orientation. In order to cover all possible scenarios for the distal hole location, two links may be provided for the Z direction, namely $L_1$ and $L_4$. As shown in FIG. 2, this pair of links can be provided to cover both lateral and medial rotations of the nail. FIG. 4 illustrates a physical implementation of an ASR, according to certain embodiments and scaled according to the dimensions set forth above.

Figure 10:
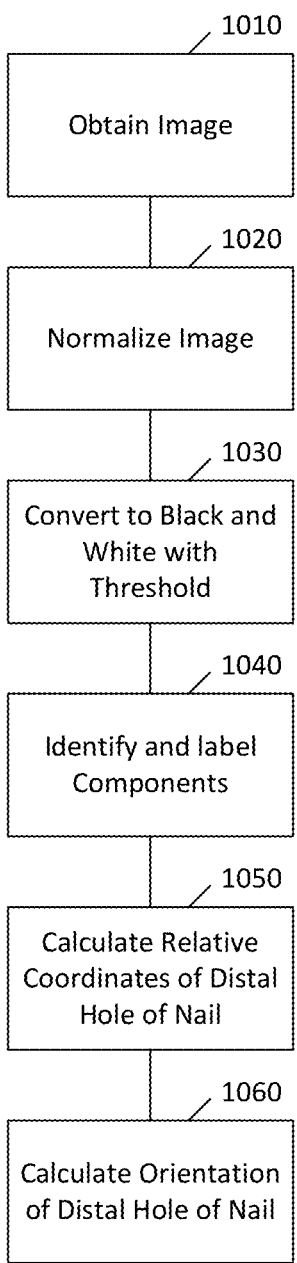
FIG. 10 illustrates a method according to certain embodiments.

Certain embodiments provide an approach for finding the location of the distal hole from the captured X-ray image of the nail, along with a probe. FIG. 10 illustrates a method according to certain embodiments.

As shown in FIG. 10, a digital imaging and communications in medicine (DICOM) image can be obtained at 1010. The DICOM image can be first normalized at 1020 and then converted to a black and white image with a specific threshold at 1030. This processing can be used to facilitate hole detection in the image by removing all unnecessary objects in the image. The unnecessary objects may, in this context, include the bone, even though the bone may be necessary from a surgical or medical standpoint.

At 1040, the connected components in the image that correspond to the probe and nail holes, along with their properties such as the component centroid location and the major and minor axis length, can be identified and labeled based on the minimum and maximum radius of the holes.

Because the exact radius of the probe holes can be known in advance, the system can readily identify which detected components correspond to the probe holes and which components correspond to the nail hole. The system can, at 1050, calculate the coordinates of the distal hole with respect to the probe hole, and consequently, $x_h$ and $y_h$ coordinates of the distal hole in the robot frame can be obtained.

Probe hole(s) may be at a predetermined or known location and orientation in the robot frame.

Figure 5:
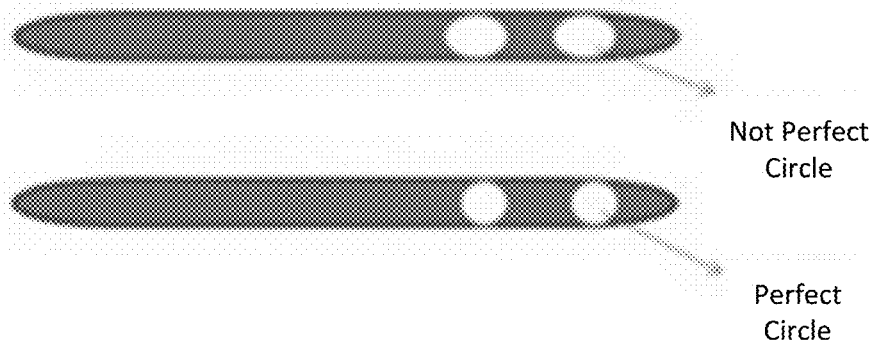
FIG. 5 illustrates perfect and non-perfect circles, according to certain embodiments.

At 1060, the orientation of the hole can be identified from the obtained X-ray image. FIG. 5 illustrates a perfect circle, according to certain embodiments. As shown in FIG. 5, for a rotated nail at top, the holes may appear as an oval in a 2D X-ray image while, at bottom, a perfect circle in the image can correspond to the case where the plane of the X-ray device is perpendicular to the distal hole. The orientation of the distal hole can be calculated using only one X-ray image using these principles.

Figure 6:
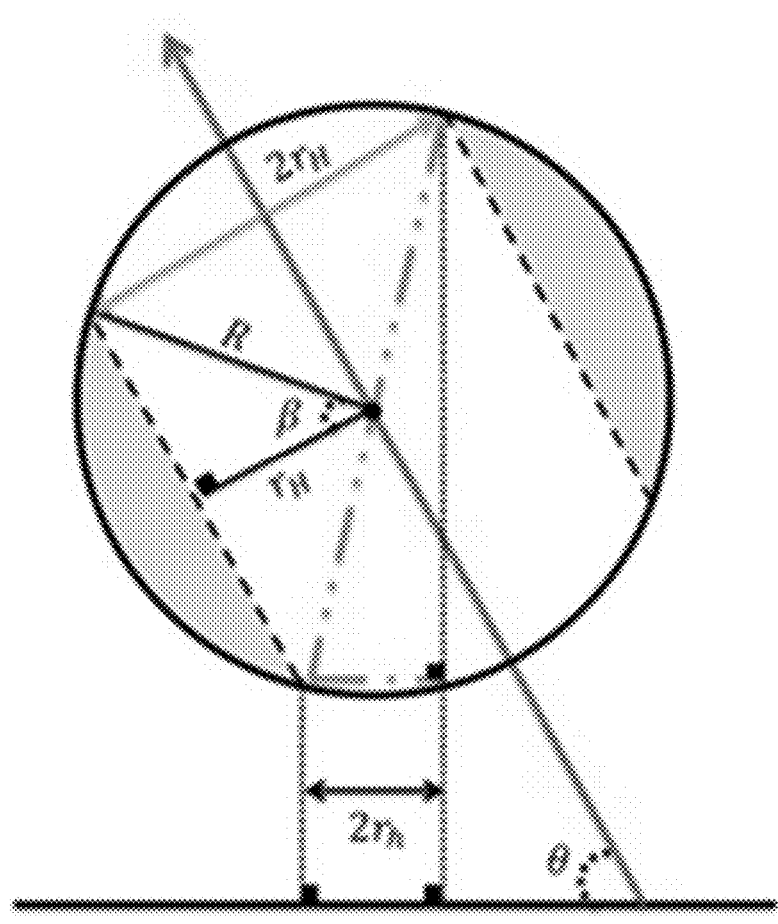
FIG. 6 illustrates a nail orientation angle calculation methodology, according to certain embodiments.

FIG. 6 illustrates a nail orientation angle calculation methodology, according to certain embodiments. FIG. 6 shows a projected distal hole in a rotated nail where $r_H$ denotes the actual hole radius, R denotes the nail radius, and $r_h$ denotes the projected hole opening in the X-ray image.

Based on the type of the nail, the system can obtain $r_H$ and R from the nail's specification. In such a case, in order to find the orientation angle of the distal hole, the system may calculate only $r_h$ from the X-ray image. Toward this, as mentioned before, the connected components in the X-ray image which correspond to the distal hole are already identified in the process of finding the location of the hole and $r_h$ can be easily calculated from the minor axis length of the identified distal hole in the X-ray image. However, this length is given in pixel and it should be transformed to the actual length in millimeter. For this, the DICOM pixel spacing information can be extracted from the X-ray DICOM info. However, in this work in order to achieve higher precision, the pixel spacing is calculated from the designed probe using the known distance between the two holes in the probe.

The method for finding the location and the orientation of distal hole has been experimentally validated using X-ray images taken in a medical clinic. Several X-rays images corresponding to different nail angles were captured using right proximal femur cancellous bone and the location and the orientation of the holes were obtained using the approach described herein. The considered holes corresponded to the proximal hole in the available bone, but the same procedures can be applied to distal holes. In certain cases, other technology may be used to locate the proximal holes, which technology may not be suitable for use in distal holes. Nevertheless, certain embodiments may be applicable to proximal holes and to distal holes.

Figure 7:
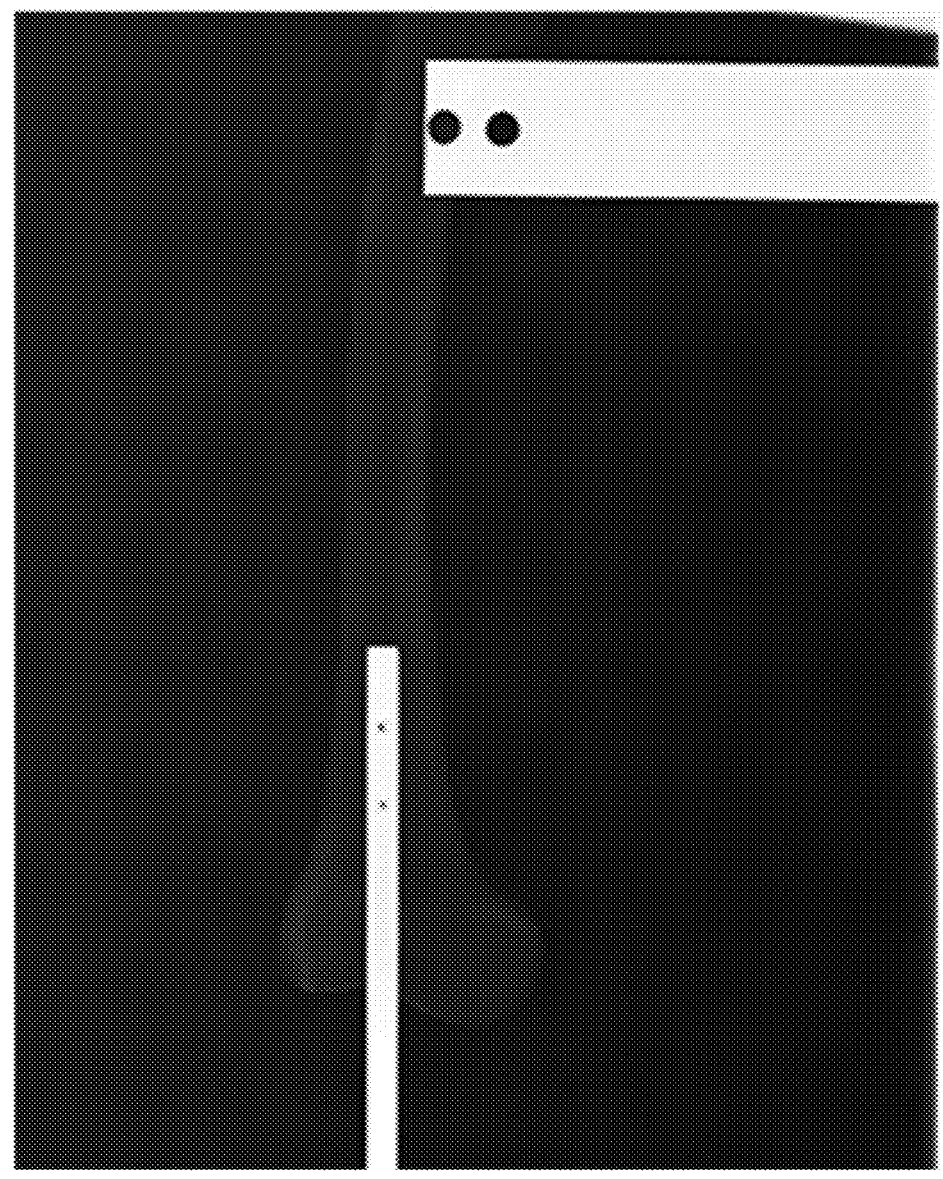
FIG. 7 illustrates an X-ray image corresponding to a 65 degree nail rotation in the ASR frame, according to certain embodiments.
Figure 8:
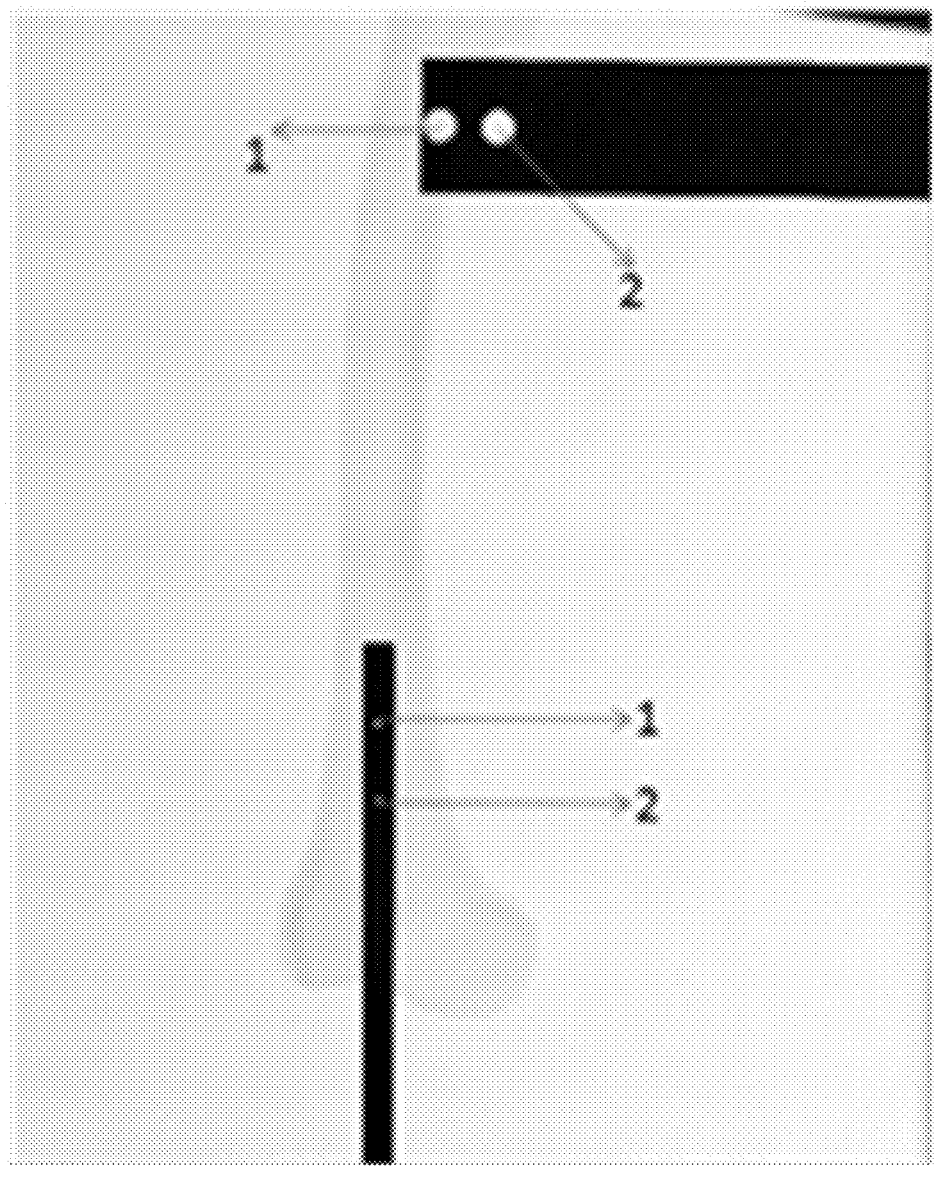
FIG. 8 illustrates an import DICOM X-ray image in MATLAB corresponding to 65 degree nail rotation in the ASR frame, according to certain embodiments.

FIG. 7 shows the captured X-ray image for the 65 degree nail rotation in the ASR frame. This figure can be imported in MATLAB using the command, dicomread. The imported image can be converted to a black/white image using the MATLAB command, im2bw. The converted imported image is shown in FIG. 8.

FIG. 11 illustrates two tables of data from an example implementation. Specifically, FIG. 11 illustrates Table 1, which provides the identified probe and distal holes corresponding to 65 degree nail rotation in the ASR frame, in a specific example. FIG. 11 also illustrates Table 2, which provides a calculated distal hole orientation for different nail rotations, in the same specific example.

Figure 9:
FIG. 9 illustrates a converted black/white X-ray image corresponding to 65 degree nail rotation in the ASR frame, according to certain embodiments.
Figure 9:

From the acquired information in Table 1 and using the fact that the distance between the designed probe holes are 22 mm, the pixel spacing denoted by "a" in the X-ray image can be calculated as $a=22/(x_{p2}-x_{p1})$ where $x_{p1}$ and $x_{p2}$ are the x coordinate of the probe holes in the X-ray image. For the image shown in FIG. 9, the pixel spacing was obtained as $a=0.151$. Next, from Table 1 and the obtained pixel spacing a, the x and y coordinates of the distal hole can be obtained with respect to the probe holes and consequently using the known coordinates of the probe holes in the ASR frame, the actual $x_h$ and $y_h$ coordinates of the distal hole in the ASR frame can be easily calculated.

From the minor axis length of the distal hole and the calculated pixel spacing, the projected hole opening parameter $r_h$ for both distal holes can be obtained. Using the approach illustrated in FIG. 6, the distal hole orientation angle can be calculated. The difference between the obtained angles for the distal holes may be due to the accuracy of the customized nail used in this experiment. The calculated distal hole orientations for different nail rotations are presented in Table 2. As demonstrated by Table 2, the hole orientations can be accurately calculated with maximum error of 1.6 degree for the first distal hole and 0.56 degree for the second distal hole. The positioning accuracy of certain embodiments may be ±0.01 mm and the orientation accuracy may be ±0.5 degree. The obtained location and orientation of the distal hole may be used by the ASR to locate and point into the distal hole in the patient body in order to do the required drilling to fix the screw in the nail.

Various embodiments may rely on software, for example for control of the assisted surgical robot. In some example embodiments, an apparatus may include or be associated with at least one software application, module, unit or entity configured as arithmetic operation(s), or as a program or portions of programs (including an added or updated software routine), which may be executed by at least one operation processor or controller. Programs, also called program products or computer programs, including software routines, applets and macros, may be stored in any apparatus-readable data storage medium and may include program instructions to perform particular tasks. A computer program product may include one or more computer-executable components that, when the program is run, are configured to carry out some example embodiments. The one or more computer-executable components may be at least one software code or portions of code. Modifications and configurations required for implementing the functionality of an example embodiment may be performed as routine(s), which may be implemented as added or updated software routine(s). In one example, software routine(s) may be downloaded into the apparatus.

As an example, software or computer program code or portions of code may be in source code form, object code form, or in some intermediate form, and may be stored in some sort of carrier, distribution medium, or computer readable medium, which may be any entity or device capable of carrying the program. Such carriers may include a record medium, computer memory, read-only memory, photoelectrical and/or electrical carrier signal, telecommunications signal, and/or software distribution package, for example. Depending on the processing power needed, the computer program may be executed in a single electronic digital computer or it may be distributed amongst a number of computers. The computer readable medium or computer readable storage medium may be a non-transitory medium.

In other example embodiments, the functionality of example embodiments may be performed by hardware or circuitry included in an apparatus, for example through the use of an application specific integrated circuit (ASIC), a programmable gate array (PGA), a field programmable gate array (FPGA), or any other combination of hardware and software. In yet another example embodiment, the functionality of example embodiments may be implemented as a signal, such as a non-tangible means, that can be carried by an electromagnetic signal downloaded from the Internet or other network.

According to an example embodiment, an apparatus, such as a node, device, or a corresponding component, may be configured as circuitry, a computer or a microprocessor, such as single-chip computer element, or as a chipset, which may include at least a memory for providing storage capacity used for arithmetic operation(s) and/or an operation processor for executing the arithmetic operation(s).

Example embodiments described herein may apply to both singular and plural implementations, regardless of whether singular or plural language is used in connection with describing certain embodiments. For example, an embodiment that describes operations of a single motor may also apply to example embodiments that include multiple instances of the motor, and vice versa.

One having ordinary skill in the art will readily understand that the example embodiments as discussed above may be practiced with procedures in a different order, and/or with hardware elements in configurations which are different than those which are disclosed. Therefore, although some embodiments have been described based upon these example embodiments, it would be apparent to those of skill in the art that certain modifications, variations, and alternative constructions would be apparent, while remaining within the spirit and scope of example embodiments.

We claim:

1. A system for robot assisted surgery, comprising:
an imaging device configured to capture an image of an implanted device and a probe, wherein the implanted device defines a hole and wherein the probe defines a hole; and
a robot comprising
at least one memory comprising computer program instructions, and
at least one processor, wherein the at least one memory and the computer program instructions are configured to, with the at least one processor, perform
obtaining a position and orientation of the hole defined by the implanted device, and

aligning a fastener to the hole defined by the implanted device using the obtained position and orientation wherein the obtaining the position and orientation of the hole defined by the implanted device comprises determining a three-dimensional position of the hole defined by the implanted device in a frame of the robot.

2. The system of claim 1, wherein the imaging device comprises an X-ray machine and the image comprises an X-ray image.

3. The system of claim 2, wherein the obtaining the position and orientation comprises obtaining the position and orientation from the image alone.

4. The system of claim 1, wherein the robot comprises a five degrees of freedom robot.

5. The system of claim 4, wherein the robot comprises four stepper motors along with a ball-screw configuration and servo motor to provide the five degrees of freedom.

6. The system of claim 1, wherein the at least one memory and the computer program instructions are configured to, with the at least one processor, perform starting or stopping the robot based on a command from a human operator.

7. The system of claim 1, wherein the obtaining the position and orientation the hole defined by the implanted device comprises comparing a portion of the image showing the hole defined by the implanted device to a portion of the image showing the hole defined by the probe.

8. The system of claim 1, wherein the obtaining the orientation of the hole defined by the implanted device comprises determining an angle of the hole along an axis defined by a bore of the hole in a frame of the robot.

9. The system of claim 1, wherein the at least one memory and the computer program instructions are configured to, with the at least one processor, perform drilling to insert the fastener into the hole based on the determined position and orientation.

10. The system of claim 1, wherein the at least one memory and the computer program instructions are configured to, with the at least one processor, perform guiding drilling to insert the fastener into the hole based on the determined position and orientation.

11. The system of claim 1, wherein the implanted device comprises an intramedullary nail.

12. A method for robot assisted surgery, comprising:

capturing, with an imaging device, an image of an implanted device and a probe, wherein the implanted device defines a hole and wherein the probe defines a hole;

obtaining, by a robot, a position and orientation of the hole defined by the implanted device; and aligning, by the robot, a fastener to the hole using the obtained position and orientation, wherein the obtaining the position and orientation of the hole defined by the implanted device comprises determining a three-dimensional position of the hole defined by the implanted device in a frame of the robot.

13. The method of claim 12, wherein the imaging device comprises an X-ray machine and the image comprises an X-ray image.

14. The method of claim 13, wherein the obtaining the position and orientation comprises obtaining the position and orientation from the image alone.

15. The method of claim 12, further comprising:

starting or stopping the robot based on a command from a human operator.

16. The method of claim 12, wherein the obtaining the position and orientation the hole defined by the implanted device comprises comparing a portion of the image showing the hole defined by the implanted device to a portion of the image showing the hole defined by the probe.

17. The method of claim 12, wherein the obtaining the orientation of the hole defined by the implanted device comprises determining an angle of the hole along an axis defined by a bore of the hole in a frame of the robot.

18. The method of claim 12, further comprising: guiding drilling to insert the fastener into the hole based on the determined position and orientation.

* * * * *